(12) United States Patent
Abbott

(10) Patent No.: US 12,042,238 B2
(45) Date of Patent: *Jul. 23, 2024

(54) COMPUTER-ASSISTED TELE-OPERATED SURGERY SYSTEMS AND METHODS

(71) Applicant: Intuitive Surgical Operations, Inc., Sunnyvale, CA (US)

(72) Inventor: Ryan Charles Abbott, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/073,026

(22) Filed: Dec. 1, 2022

(65) Prior Publication Data

US 2023/0093215 A1    Mar. 23, 2023

Related U.S. Application Data

(63) Continuation of application No. 16/636,269, filed as application No. PCT/US2018/044961 on Aug. 2, 2018, now Pat. No. 11,517,383.

(51) Int. Cl.
*B25J 9/04* (2006.01)
*A61B 34/00* (2016.01)
(Continued)

(52) U.S. Cl.
CPC .............. *A61B 34/35* (2016.02); *A61B 34/25* (2016.02); *A61B 34/70* (2016.02); *B25J 9/04* (2013.01);
(Continued)

(58) Field of Classification Search
CPC .. B25J 9/1689; B25J 9/04; B25J 18/04; A61B 34/25; A61B 34/37; A61B 34/35; A61B 34/70; A61B 90/11
See application file for complete search history.

(56) References Cited

U.S. PATENT DOCUMENTS 5,397,323 A    3/1995    Taylor et al.
6,451,027 B1    9/2002    Cooper et al.
(Continued)

FOREIGN PATENT DOCUMENTS

WO    WO-2014201340 A1    12/2014
WO    WO-2015175200 A1    11/2015
(Continued)

OTHER PUBLICATIONS

Berkelman et al., A compact, compliant laparoscopic endoscope manipulator, 2002, IEEE, p. 1870-1875 (Year: 2002).*
(Continued)

*Primary Examiner* — Mcdieunel Marc
(74) *Attorney, Agent, or Firm* — MARSHALL, GERSTEIN & BORUN LLP

(57) ABSTRACT

Manipulator devices are used for computer-assisted tele-operated surgery. In some embodiments, the manipulator devices described herein include an arm with a proximal end that is configured to releasably couple with a set-up structure of a computer-assisted tele-operated surgery system. A first ring is rotatably coupled to a distal end portion the arm and is rotatably driven by a first gear motor within the arm. A second ring that is concentric with the first ring is also rotatably coupled to the distal end portion of the arm. Rotations of the second ring are driven by a second gear motor within the arm. An instrument actuator coupling is pivotably coupled to the second ring. The instrument actuator coupling is configured to releasably couple with a computer-assisted tele-operated surgical instrument actuator, and defines a surgical instrument insertion axis.

18 Claims, 8 Drawing Sheets

(51) Int. Cl.
*A61B 34/35* (2016.01)
*B25J 9/16* (2006.01)
*B25J 18/04* (2006.01)
*A61B 34/30* (2016.01)

(52) U.S. Cl.
CPC .............. *B25J 9/1689* (2013.01); *B25J 18/04* (2013.01); *A61B 2034/301* (2016.02); *A61B 2034/305* (2016.02)

(56) References Cited

U.S. PATENT DOCUMENTS

| | | | |
|---|---|---|---|
| 6,728,599 B2* | 4/2004 | Wang | A61B 34/70 600/595 |
| 8,151,661 B2 | 4/2012 | Schena et al. | |
| 11,517,383 B2* | 12/2022 | Abbott | A61B 34/35 |
| 2004/0024387 A1* | 2/2004 | Payandeh | A61B 90/11 606/1 |
| 2009/0088775 A1* | 4/2009 | Swarup | A61B 34/71 700/264 |
| 2009/0157092 A1* | 6/2009 | Blumenkranz | A61B 90/06 73/800 |
| 2010/0204713 A1 | 8/2010 | Ruiz Morales | |
| 2011/0015650 A1 | 1/2011 | Choi et al. | |
| 2011/0023285 A1* | 2/2011 | Cooper | A61B 34/71 29/428 |
| 2011/0213383 A1 | 9/2011 | Lee et al. | |
| 2013/0103051 A1 | 4/2013 | Cooper et al. | |
| 2014/0188130 A1 | 7/2014 | Sanchez et al. | |
| 2014/0276950 A1* | 9/2014 | Smaby | G06F 16/113 606/130 |
| 2015/0196365 A1 | 7/2015 | Kostrzewski et al. | |
| 2016/0235490 A1 | 8/2016 | Srivastava et al. | |
| 2017/0020615 A1 | 1/2017 | Koenig et al. | |
| 2018/0049737 A1 | 2/2018 | Swayze et al. | |
| 2018/0256235 A1* | 9/2018 | Cohen | A61B 90/98 |

FOREIGN PATENT DOCUMENTS

| | | |
|---|---|---|
| WO | WO-2016043845 A1 | 3/2016 |
| WO | WO-2016064616 A1 | 4/2016 |
| WO | WO-2016090459 A1 | 6/2016 |
| WO | WO-2016144998 A1 | 9/2016 |
| WO | WO-2016183054 A1 | 11/2016 |

OTHER PUBLICATIONS

Shang et al., A Single-Port Robotic System for Transanal Microsurgery—Design and Validation, 2017, IEEE, p. 1510-1517 (Year: 2017).*
Direkwatana et al., Development of wire-driven laparoscopic surgical robotic system, "MU-LapaRobot" 2011, IEEE, p. 485-490 (Year: 2011).*
Gosselin et al., Design of a High Fidelity Haptic Device for Telesurgery, 2006, IEEE, p. 205-210 (Year: 2006).*
Berkelman P., et al., "Control and User Interface Design for Compact Manipulators in Minimally-invasive Surgery," IEEE, Aug. 2005, pp. 25-30.
Direkwatana C., et al., "Development of Wire-driven Laparoscopic Surgical Robotic System, "MU-LapaRobot"," IEEE, Dec. 2011, pp. 485-490.
Gosselin F., et al., "Design of a High Fidelity Haptic Device for Telesurgery," IEEE, Apr. 2005, pp. 205-210.
International Search Report and Written Opinion for Application No. PCT/US2017/051846, mailed on Jan. 10, 2018, 11 pages.
International Search Report and Written Opinion for Application No. PCT/US2018/044961, mailed on Nov. 26, 2019, 9 pages.
Long J.A., et al., "Development of Miniaturized Light Endoscope-holder Robot for Laparoscopic Surgery," Journal of Endourology, Aug. 2007, vol. 21 (8), pp. 911-914.
Shang J., et al., "A Single-port Robotic System for Transanal Microsurgery—design and Validation," IEEE, Jan. 2017, pp. 1510-1517.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

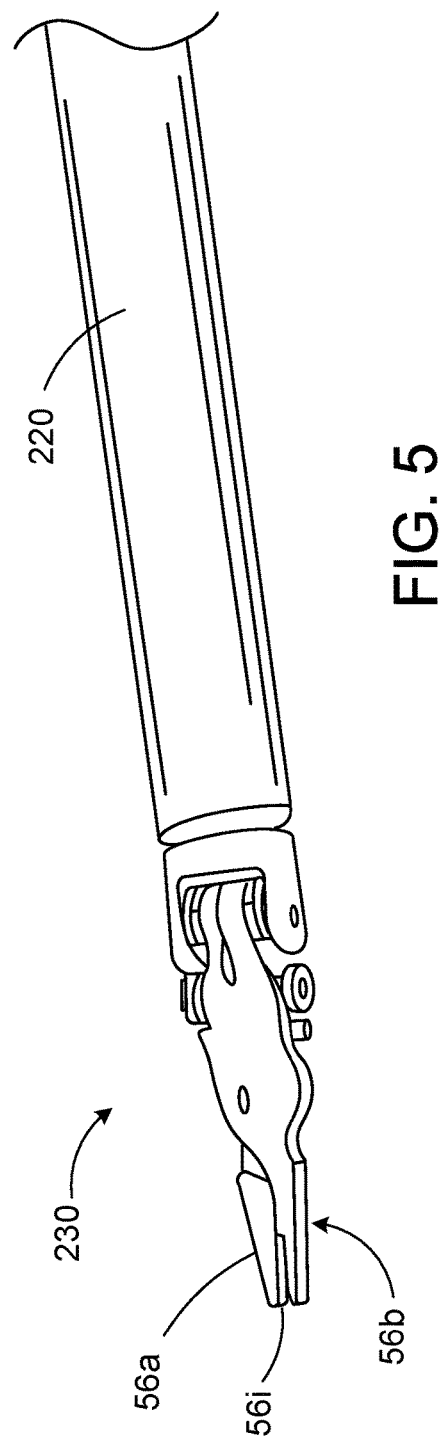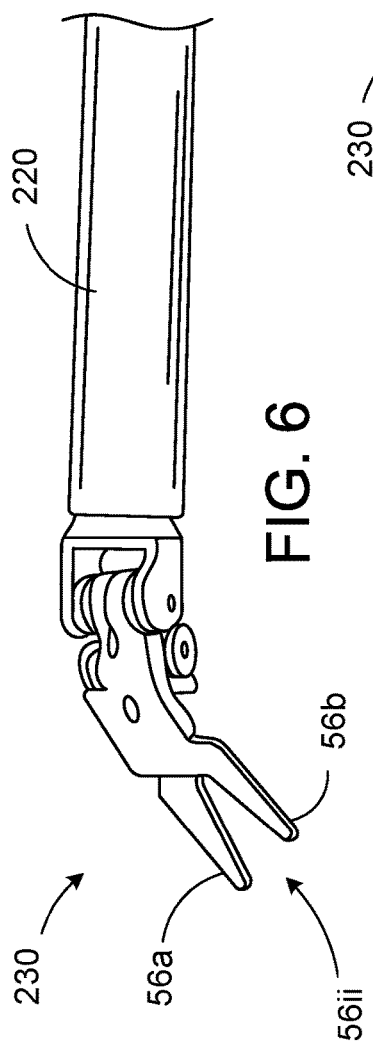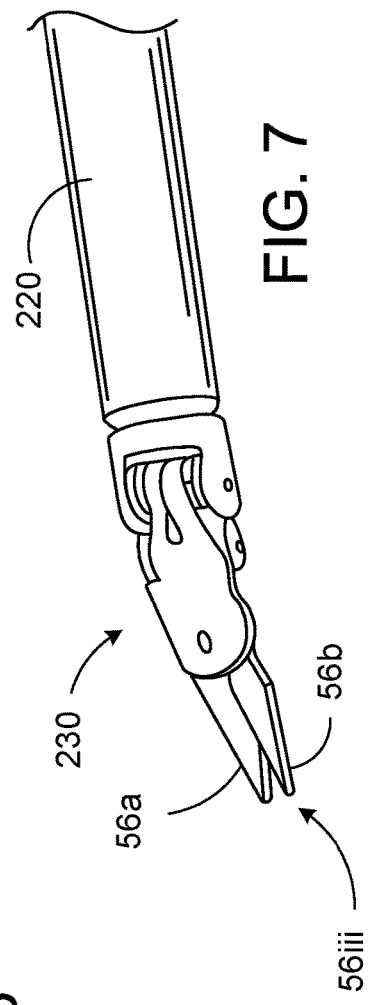

COMPUTER-ASSISTED TELE-OPERATED SURGERY SYSTEMS AND METHODS

RELATED APPLICATIONS

This application is a continuation of U.S. application Ser. No. 16/636,269 (U.S. Pat. No. 11,517,383), filed on Feb. 3, 2020, which is a U.S. National Stage Application under 35 U.S.C. § 371 and claims the benefit of International Patent Application Serial No. PCT/US2018/044961, filed on Aug. 2, 2018, which claims the benefit of priority to U.S. Provisional Patent Application No. 62/541,320, filed Aug. 4, 2017. The entire contents of each of the foregoing applications are incorporated herein by reference.

TECHNICAL FIELD

This disclosure relates to devices and methods for minimally invasive computer-assisted tele-operated surgery. For example, this disclosure relates to manipulator devices for a computer-assisted tele-operated surgery system.

BACKGROUND

Robotic systems and computer-assisted devices often include multiple robots or movable arms to manipulate instruments for performing a task at a surgical work site and at least one robot or movable arm for supporting an image capturing device which captures images of the surgical work site. A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic-controlled surgical instruments can be inserted through small, minimally invasive surgical apertures or natural orifices to treat tissues at surgical sites within the patient, often avoiding the trauma generally associated with accessing a surgical worksite by open surgery techniques. These computer-assisted tele-operated systems can move the working ends (end effectors) of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

This disclosure describes devices and methods for minimally invasive robotic surgery using a computer-assisted tele-operated surgery device. For example, this disclosure describes manipulator devices for a computer-assisted tele-operated surgery system. In some embodiments, the manipulator devices include an arm with a proximal (away from the patient) end that is configured to releasably couple with a set-up structure of a computer-assisted tele-operated surgery system. A first ring is rotatably coupled to a distal (towards the patient) end portion the arm. Rotations of the first ring are driven by a first gear motor within the arm. A second ring that is concentric with the first ring is also rotatably coupled to the distal end portion of the arm. Rotations of the second ring are driven by a second gear motor within the arm. An instrument actuator coupling is pivotably coupled to the second ring. The instrument actuator coupling is configured to releasably couple with a computer-assisted tele-operated surgical instrument actuator, and defines a surgical instrument insertion axis.

In one aspect, this disclosure is directed to a computer-assisted tele-operated surgery manipulator that includes an arm configured to releasably couple with a set-up structure of a computer-assisted tele-operated surgery system; a first ring rotatably coupled to the arm; a second ring rotatably coupled to the arm; and an instrument actuator coupling pivotably coupled to the second ring and defining an instrument insertion axis. The first ring and the second ring are arranged concentrically. The instrument actuator coupling is configured to releasably couple with a computer-assisted tele-operated surgical instrument actuator.

Such a computer-assisted tele-operated surgery manipulator may optionally include one or more of the following features. The manipulator may also include a first ring drive motor coupled to drive rotations of the first ring and a second ring drive motor coupled to drive rotations of the second ring. The first ring and the second ring may be rotatable relative to each other. The instrument actuator coupling may be pivotably coupled to the second ring about a tilt axis that is canted in relation to the insertion axis. The instrument actuator coupling may be pivotably coupled to the second ring about a tilt axis that is canted in relation to a central axis shared by the first ring and the second ring. The tilt axis and the central axis shared by the first ring and the second ring may intersect at a remote center of motion point. The point of remote center of motion may remain fixed in space at all possible rotational orientations of the first ring and the second ring. The second ring may be configured to releasably couple with a cannula configured for providing surgical access through a patient's body wall during surgery using the computer-assisted tele-operated surgery manipulator device. The instrument actuator coupling may include a roll-adjustment motor for rotatably driving a computer-assisted tele-operated surgical instrument actuator about the instrument insertion axis.

In another aspect, this disclosure is directed to another computer-assisted tele-operated surgery manipulator that includes: an arm configured to releasably couple with a set-up structure of a computer-assisted tele-operated surgery system; two concentrically-arranged rings rotatably coupled to the arm and rotatable in relation to each other about a central axis; and a computer-assisted tele-operated surgical instrument actuator pivotably coupled to a first one of the rings about a tilt axis.

Such a manipulator may optionally include one or more of the following features. The surgical instrument actuator may be geared to a second one of the rings. Differential relative rotations of the rings may drive pivoting of the surgical instrument actuator about the tilt axis. The manipulator may also include two drive motors. Each of the drive motors may be coupled to drive rotations of a respective one of the rings. The tilt axis may be canted in relation to the central axis. The tilt axis and the central axis may intersect at a remote center of motion point. The point of remote center of motion may remain fixed in space at all possible rotational orientations of the rings. A second one of the rings may be configured to releasably couple with a cannula configured for providing surgical access through a patient's body wall during surgery using the computer-assisted tele-operated surgery manipulator device. The manipulator may also include a roll-adjustment motor for rotatably driving the surgical instrument actuator about an instrument insertion axis.

In another aspect, this disclosure is directed to a computer-assisted tele-operated surgery system that includes: (i) a set-up structure releasably coupleable with a support structure; (ii) a computer-assisted tele-operated surgery manipulator: and (iii) a computer-assisted tele-operated surgical instrument actuator. The manipulator includes an arm releasably coupleable with the set-up structure, and two concentrically-arranged rings rotatably coupled to the arm and rotatable in relation to each other about a central axis. The surgical instrument actuator is pivotably coupled to a first one of the rings about a tilt axis. The set-up structure includes a bracket with one or more joints.

Such a system may optionally also include a surgical instrument releasably coupleable with the surgical instrument actuator.

Some or all of the embodiments described herein may provide one or more of the following advantages. In some cases, the tele-operated surgical manipulator devices provided herein are advantageously structured to have a low-profile, i.e., to be spatially-compact. Such a compact configuration is advantageous in that the working space occupied by the tele-operated surgical manipulators above the patient is minimized, allowing for enhanced patient access by the surgical team. Additionally, greater visualization of the patient and communications between the surgical team members is facilitated by the compact manipulator working space.

In some embodiments, the tele-operated surgical manipulator devices provided herein are advantageously structured to have a remote center of motion that is close to the manipulator. Accordingly, the manipulator can be located closely to the patient (e.g., within 2 cm, within 3 cm, within 4 cm, within 5 cm, within 7 cm, or within 10 cm) to save space.

Further, lessening the size of the manipulator working space can reduce the potential for collisions between manipulators. In result, the need for redundant degrees of freedom of the manipulators is mitigated. Hence, the complexity of the manipulators can be lessened in some cases.

The compact size of the tele-operated surgical manipulator devices provided herein can also advantageously facilitate mounting the manipulators to a rail of an operating table in some cases. In such a case, as the operating table is manipulated to enhance surgical access, the table-mounted manipulator devices inherently follow. Therefore, the need to reposition the manipulators in response to movements of the operating table is advantageously reduced or eliminated.

In addition, the tele-operated surgical manipulator devices provided herein are advantageously structured to have a relatively low mass and inertia. In addition, the mass distribution is substantially constant such that the inertia is substantially constant, and therefore predictable.

The details of one or more embodiments are set forth in the accompanying drawings and the description below.

Other features, objects, and advantages will be apparent from the description and drawings, and from the claims.

BRIEF DESCRIPTION OF THE DRAWINGS

FIG. 5 is a perspective view of a distal end portion of an example surgical instrument in a first configuration.

FIG. 6 is a perspective view of the distal end portion of the surgical instrument of FIG. 5 in a second configuration.

FIG. 7 is a perspective view of the distal end portion of the surgical instrument of FIG. 5 in a third configuration.

Like reference symbols in the various drawings indicate like elements.

DETAILED DESCRIPTION

Figure 2:
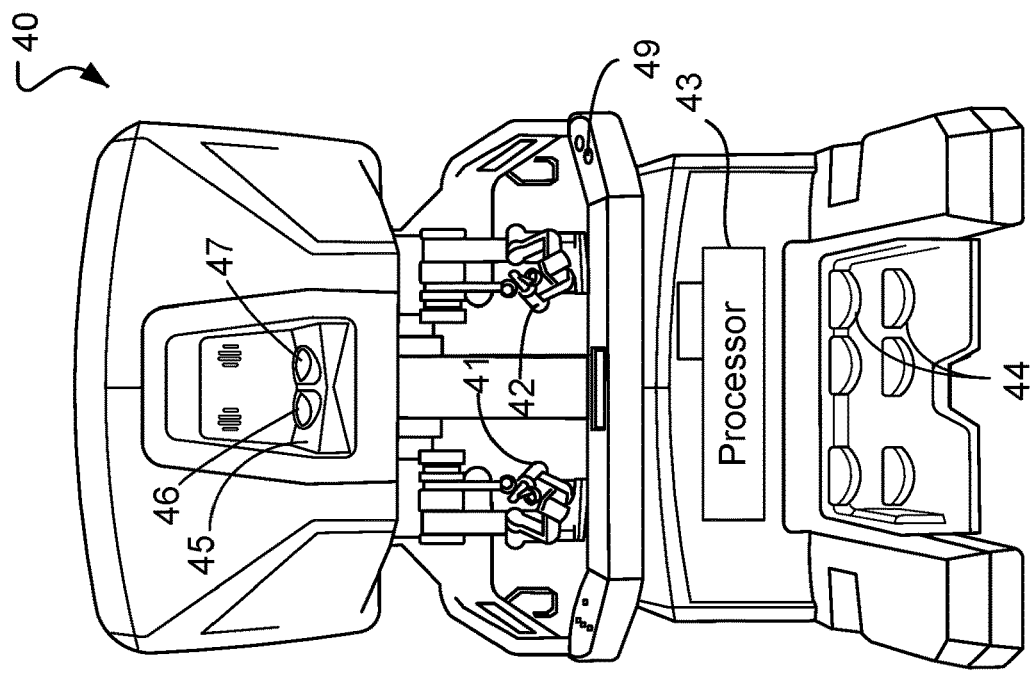
FIG. 2 is a front view of an example surgeon console of a computer-assisted tele-operated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., Nitinol, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention are described primarily in terms of an implementation using a da Vinci® Surgical System, commercialized by Intuitive Surgical, Inc. of Sunnyvale, Calif. Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure describes improved surgical and robotic devices, systems, and methods. The inventive concepts are particularly advantageous for use with computer-assisted teleoperated surgical systems (which may be referred to as "surgical robotic systems") in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery, movement of the manipulator assembly may be controlled by one or more processors (or simply "a processor") of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Figure 1:
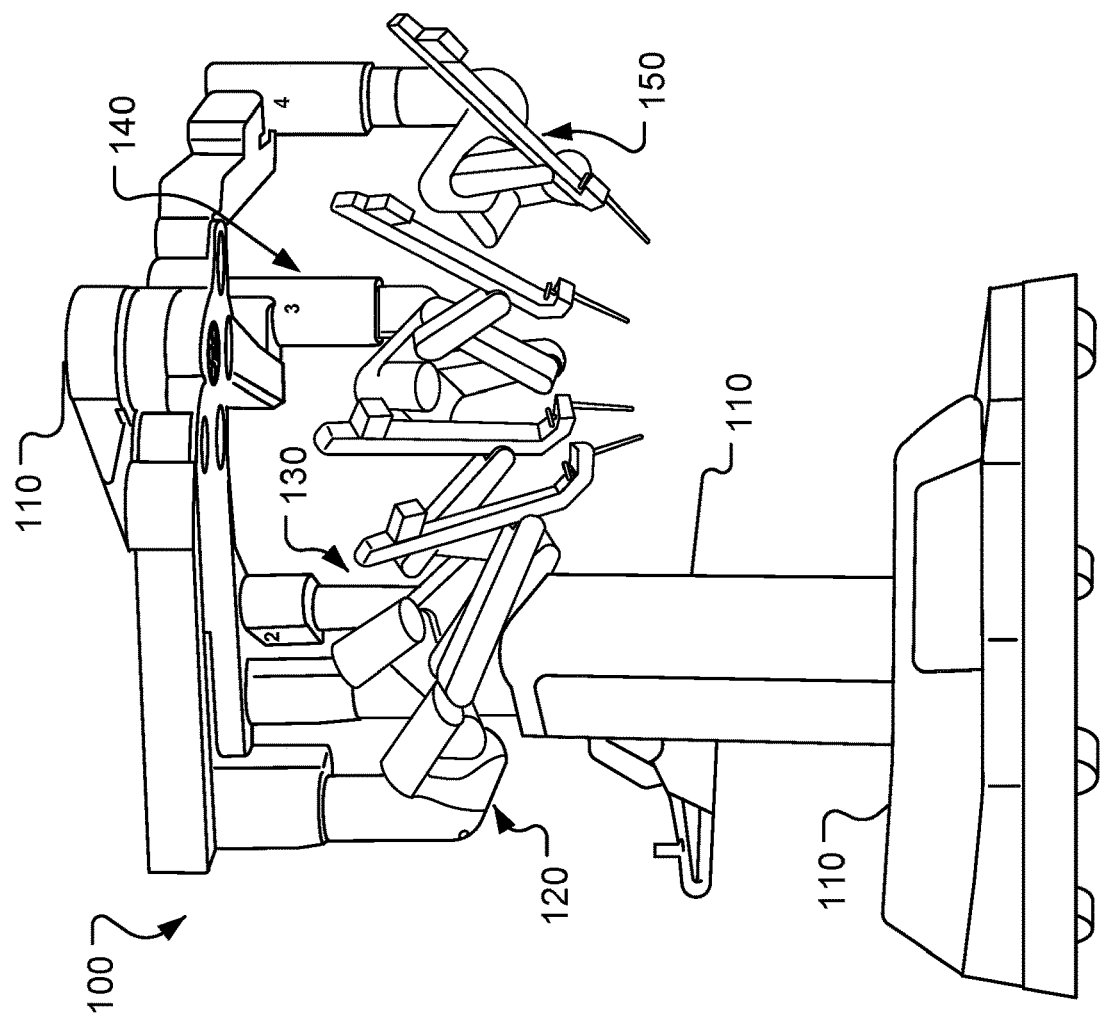
FIG. 1 is a perspective view of an example patient-side cart of a computer-assisted tele-operated surgery system.

Referring to FIGS. 1 and 2, computer-assisted surgery systems for minimally invasive telesurgery (or "computer-assisted robotic systems") can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120 (or "manipulator assembly 120"), a second robotic manipulator arm assembly 130 (or "manipulator assembly 130"), a third robotic manipulator arm assembly 140 (or "manipulator assembly 140"), and a fourth robotic manipulator arm assembly 150 (or "manipulator assembly 150"). Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control, using the processor(s) of the surgery system, the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 (and other "processors" described herein) may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the telesurgery system.

The processor 43 (and the processors of the other surgery systems described herein) can execute machine-readable instructions from non-transitory machine-readable media that activate the processor 43 to perform actions corresponding to the instructions. Accordingly, it should be understood that the disclosure of computer-assisted surgery techniques and methods herein includes a concomitant disclosure of non-transitory machine-readable media comprising corresponding machine-readable instructions.

Figure 3:
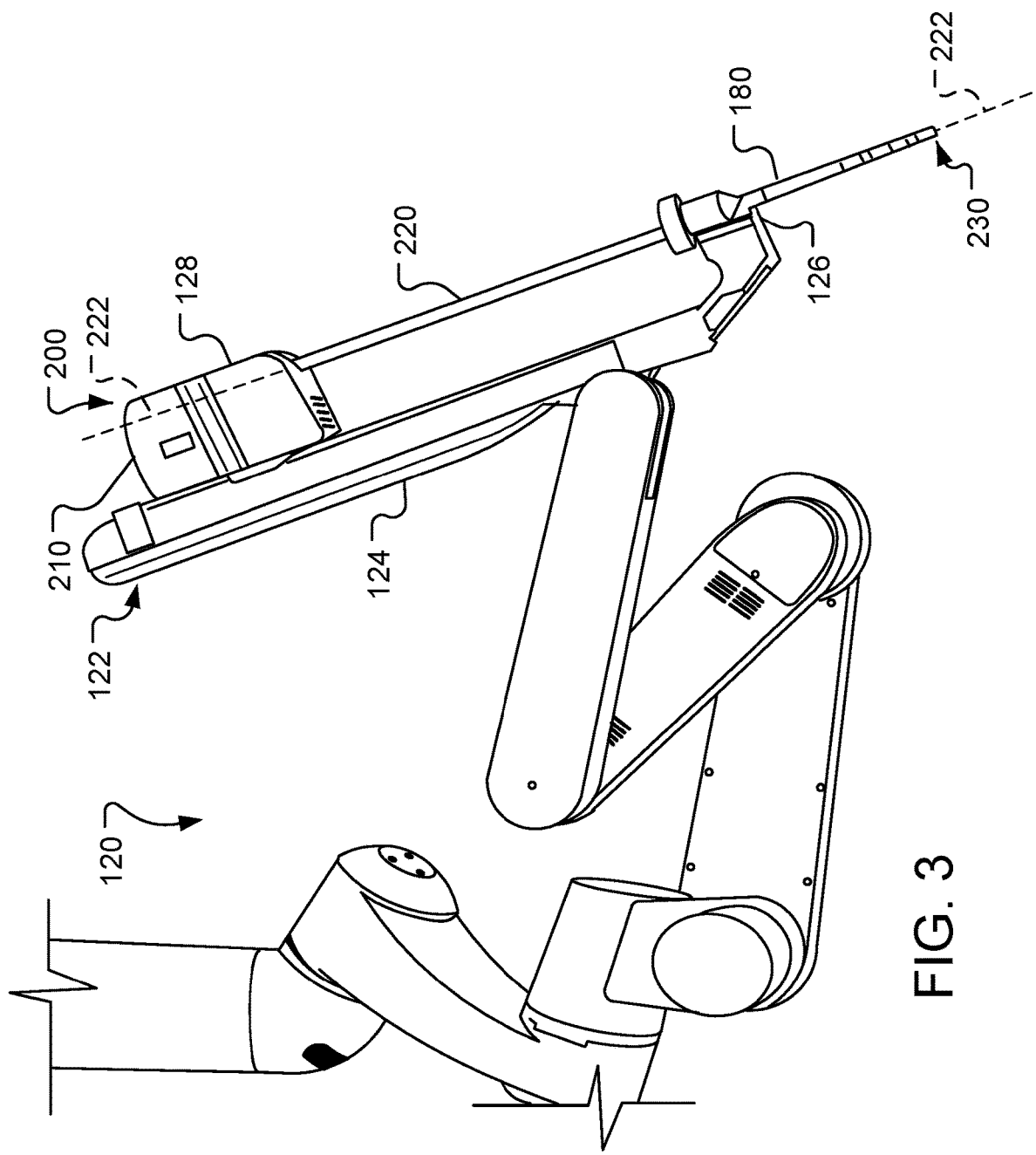
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. In some embodiments, a processor of the surgery systems described herein is configured to detect a releasable coupling of the cannula 180 to the manipulator assembly 120, for example.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably coupleable with the instrument holder carriage 128. The shaft 220 extends distally from the transmission assembly 210. The end effector 230 is disposed at a distal end of the shaft 220. In some embodiments, a processor of the surgery systems described herein is configured to detect an installation of the surgical instrument 200 to the manipulator assembly 120, for example.

The shaft 220 defines a longitudinal axis 222 that is coincident with a longitudinal axis of the cannula 180, and is coincident with a longitudinal axis of the lumen defined by the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
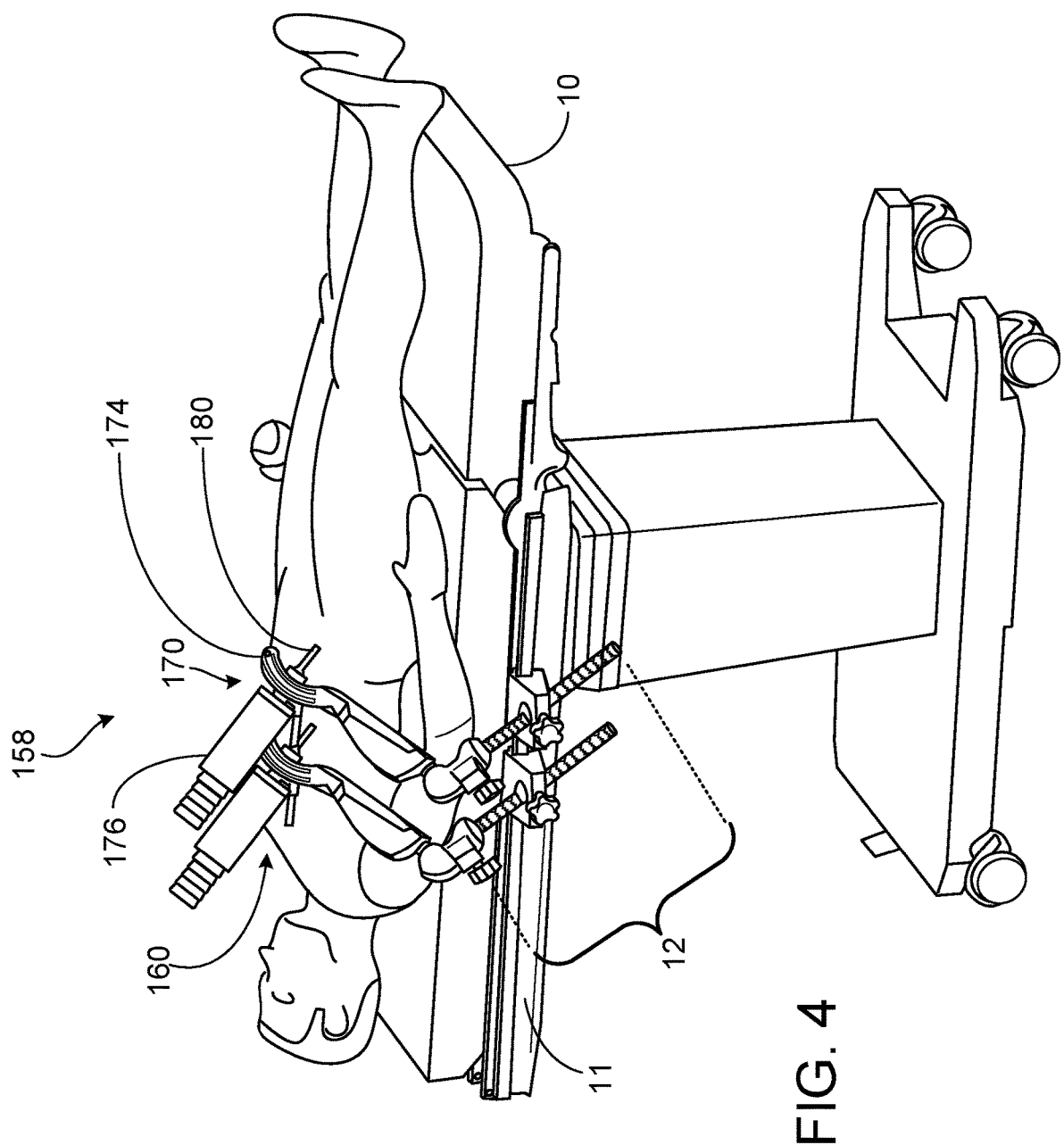
FIG. 4 is a perspective view of another type of patient-side computer-assisted tele-operated surgery system.

Also referring to FIG. 4, another example patient-side system 158 for minimally invasive surgery includes a first computer-assisted tele-operated system 160 and a second computer-assisted tele-operated system 170 that are each mounted to a rail 11 of an operating table 10. In some cases, this configuration of patient-side system 158 can be used as an alternative to the patient-side cart 100 of FIG. 1. While only two computer-assisted tele-operated systems 160 and 170 are depicted, it should be understood that more than two (e.g., three, four, five, six, and more than six) can be included in some configurations. The second computer-assisted tele-operated system 170 will be described in detail. The description of the second computer-assisted tele-operated system 170 also applies to the first computer-assisted tele-operated system 160.

The computer-assisted tele-operated system 170 includes a set-up structure 172, a manipulator device 174, a surgical instrument actuator 176, a surgical instrument or endoscope (not shown; refer to FIG. 8), and a cannula 180. In the depicted embodiment, the set-up structure 172 is adjustable and releasably coupled with the rail 11 of the operating table 10. The manipulator device 174 is releasably coupled to the set-up structure 172. The surgical instrument actuator 176 is releasably coupled to the manipulator device 174 via an instrument actuator coupling as described further below. The cannula 180 is also releasably coupled to the manipulator device 174. The cannula 180 extends through a body wall opening of the patient.

In the depicted embodiment, the joints of the set-up structure 172 are manually adjustable. The set-up structure 172 has multiple degrees of freedom, and can be fixed stationary in a desired configuration. While in the depicted embodiment the set-up structure 172 is rail-mounted to a support structure, in some embodiments the set-up structure 172 is mounted otherwise to a support structure, such as, but not limited to, on an overhead frame, from a floor, and the like.

In some cases, the operating table 10 (and the rail 11) may be moved or reconfigured during the surgery. For example, in some cases, the operating table 10 may be tilted about various axes, raised, lowered, pivoted, rotated, and the like. In some cases, by manipulating the orientation of the operating table 10, the clinicians can utilize the effects of gravity to position internal organs of the patient in positions that facilitate enhanced surgical access. In some cases, such movements of the operating table 10 may be integrated as a part of the computer-assisted tele-operated surgery system, and controlled by the system. As the operating table 10 is moved, the first computer-assisted tele-operated system 160 and the second computer-assisted tele-operated system 170 inherently move along with the operating table 10 and maintain their spatial relationships to the operating table 10.

Also referring to FIGS. 5-7, a variety of alternative computer-assisted tele-operated surgical instruments of different types and differing end effectors 230 may be used, with the instruments of at least some of the manipulators being removed and replaced during a surgical procedure. Several of these end effectors, including, for example, DeBakey Forceps 56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

In some cases, the computer-assisted tele-operated surgical instruments include multiple degrees of freedom such as, but not limited to, roll, pitch, yaw, insertion depth, opening/closing of jaws, actuation of staple delivery, activation of electro-cautery, and the like. At least some of such degrees of freedom can be actuated by an instrument drive system to which the surgical instrument can be selectively coupled.

The elongate shaft 220 allow the end effector 230 and the distal end of the shaft 220 to be inserted distally into a surgical worksite through a minimally invasive aperture (via cannula 180), often through a body wall (e.g., abdominal wall) or the like. In some cases, a body wall retractor member on a distal end of the cannula 180 can be used to tent the body wall, thereby increasing the surgical workspace size. In some cases, the surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Figure 8:
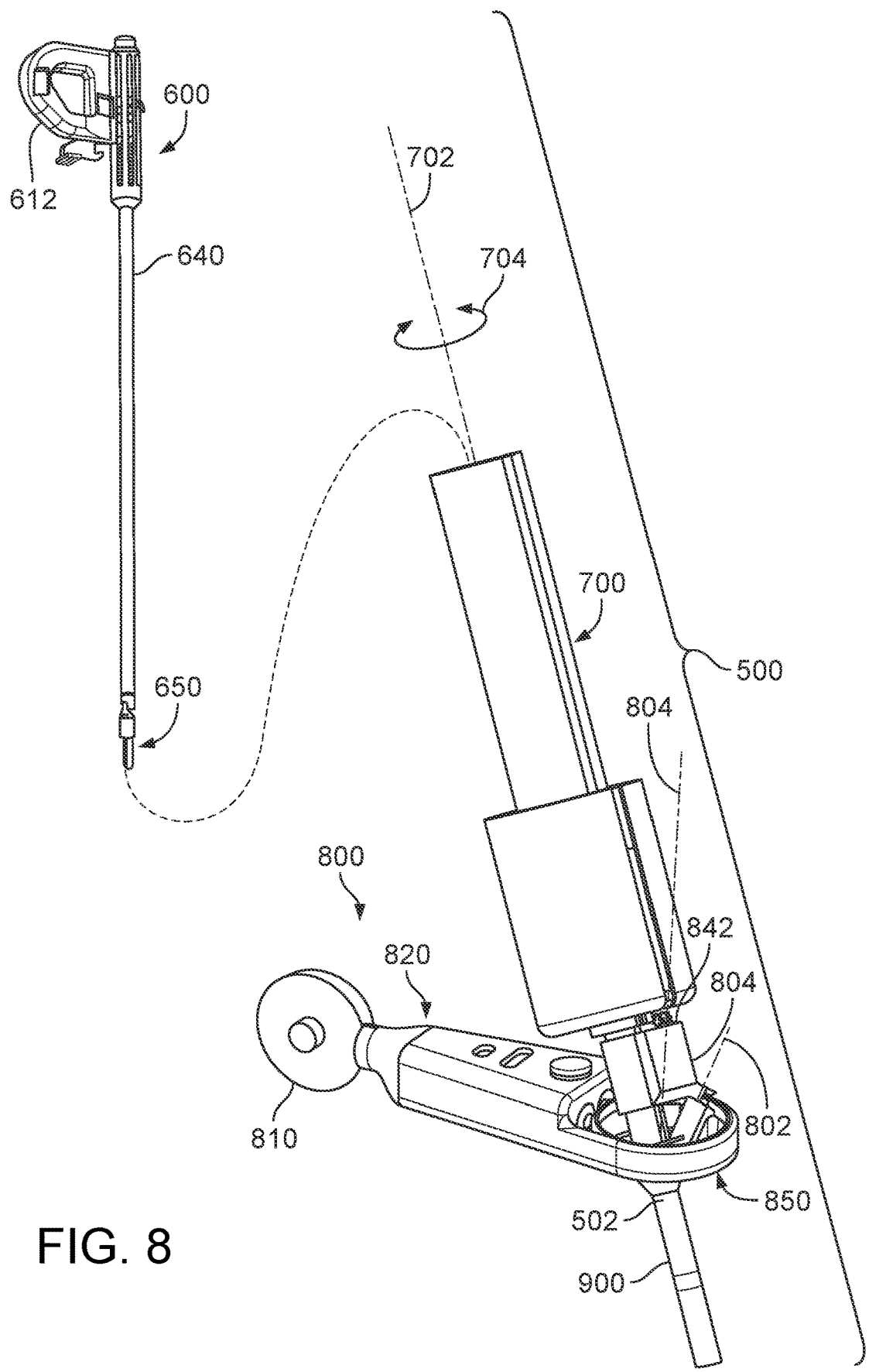
FIG. 8 is an exploded perspective view depicting a surgical instrument that can couple with a surgical instrument actuator that is mounted to an example computer-assisted tele-operated surgery manipulator device in accordance with some embodiments.

Referring to FIG. 8, an example computer-assisted tele-operated surgery system 500 includes a surgical instrument 600 that is selectively coupleable with a compatible surgical instrument actuator 700 (also referred to herein as a "surgical instrument actuator pod," or a "pod") that is, in turn, coupled to an example manipulator assembly 800 (also referred to herein as a "manipulator device" or a "manipulator"). In some embodiments, the surgical instrument actuator 700 is readily detachable from the manipulator assembly 800 such that the surgical instrument actuator 700 can be conveniently interchanged with another pod. The manipulator assembly 800 can be adjustably mounted to a frame or a structure (such as the set-up structure 172 of FIG. 4).

When the surgical instrument 600 is coupled with the surgical instrument actuator 700, a shaft 640 of the surgical instrument 600 slidably extends through a cannula 900 that is releasably coupled to the manipulator assembly 800. In use, the cannula 900 can extend through a body wall of a patient. The surgical instrument 600 includes an end effector 650 that is controlled by the surgeon performing the computer-assisted tele-operated surgery.

The surgical instrument actuator 700 defines a space configured to receive the surgical instrument 600. When the surgical instrument 600 is coupled with the surgical instrument actuator 700, the surgical instrument actuator 700 can actuate movements of the end effector 650, and of the surgical instrument 600 as a whole. For example, the surgical instrument actuator 700 can actuate translational movements of the surgical instrument along the longitudinal axis 702 of the surgical instrument actuator 700. That is, the surgical instrument actuator 700 can insert and retract the surgical instrument 600 deeper and shallower in relation to the patient. Hence, the longitudinal axis 702 may also be referred to as the insertion axis 702.

Broadly speaking, the manipulator assembly 800 includes a mounting base 810, an arm 820, an instrument actuator coupling 840, and a pair of concentric rings 850. The mounting base 810 is configured to releasably couple with a set-up structure of a computer assisted tele-operated surgery system (such as the set-up structure 172 of FIG. 4). In some embodiments, the arm 820 is rotatably coupled to the mounting base 810.

The instrument actuator coupling 840 is configured to releasably couple with the surgical instrument actuator 700, and is movably coupled with the arm 820 (via the pair of concentric rings 850 as described further below) such that the instrument actuator coupling 840 can be rotated and tilted in relation to the arm 820. As the instrument actuator coupling 840 is rotated and/or tilted in relation to the arm 820, the orientation of the insertion axis 702 is moved in space so that the end effector 650 can be positioned anywhere within a working envelop as the surgeon desires.

The computer-assisted tele-operated surgery system 500 is configured to actuate motions of the surgical instrument 600 in response to input (e.g., surgeon input using the surgeon console 40 and processor 43 as described in reference to FIG. 2). For example, the surgical instrument actuator 700 is rotatable in relation to the arm 820 by a roll motor 842 coupled to the instrument actuator coupling 840. That is, the roll motor 842 mounted to the instrument actuator coupling 840 can actuate roll motions of the surgical instrument actuator 700 (and the surgical instrument 600) about the insertion axis 702 as indicated by arrow 704. In addition, rotations of the pair of concentric rings 850, either individually or jointly, causes the instrument actuator coupling 840 (and the surgical instrument actuator 700 and the surgical instrument 600) to rotate and/or tilt in relation to the arm 820. Such tilting motions of the instrument actuator coupling 840 are made about a tilt axis 802. The tilt axis 802, which is canted (nonparallel), in relation to the insertion axis 702 and to a central axis 804 of the pair of concentric rings 850, is defined by the pivotable coupling mechanism by which the instrument actuator coupling 840 is coupled to the pair of concentric rings 850, as described further below.

In some embodiments (such as the depicted embodiment), the insertion axis 702, the central axis 804 of the pair of concentric rings 850, and the tilt axis 802 intersect each other at a point in space referred to as a remote center of motion 502. The remote center of motion 502 is a point in space around which the roll, pitch, and yaw motions described above are made. For example, as the surgical instrument actuator 700 is rotated in relation to the arm 820 about the insertion axis 702 to generate a roll motion of the surgical instrument 600, the position of the remote center of motion 502 is unchanged because the insertion axis 702 passes through the remote center of motion 502. Also, as the instrument actuator coupling 840 (as well as the surgical instrument actuator 700 and surgical instrument 600) tilts by pivoting around the tilt axis 802, the position of the remote center of motion 502 is unchanged because the tilt axis 802 passes through the remote center of motion 502. Still further, as the instrument actuator coupling 840 (as well as the surgical instrument actuator 700 and surgical instrument 600) rotates about the central axis 804 of the pair of concentric rings 850, the position of the remote center of motion 502 is unchanged because the central axis 804 of the pair of concentric rings 850 passes through the remote center of motion 502. Hence, it can be said that the computer-assisted tele-operated surgery system 500 is a hardware-constrained remote center of motion system.

In use, the remote center of motion 502 (which is typically at a location coincident with a region of the cannula 900) may be positioned at the body wall of the patient. One advantage of such an arrangement is that while the surgical instrument 600 undergoes roll, pitch, and yaw motions, the resulting stress applied to the body wall by the cannula 900 is negligible because the portion of the cannula 900 (at the remote center of motion 502) that interfaces with the body wall remains substantially stationary even while the surgical instrument 600 undergoes the roll, pitch, and yaw motions.

Further, in regard to the hardware-constrained remote center of motion, it should be understood that at all positions and orientations of the instrument actuator coupling 840 (as well as the surgical instrument actuator 700 and surgical instrument 600), the insertion axis 702, the tilt axis 802, and the central axis 804 of the pair of concentric rings 850 intersect each other where the remote center of motion 502 is located.

Figure 9:
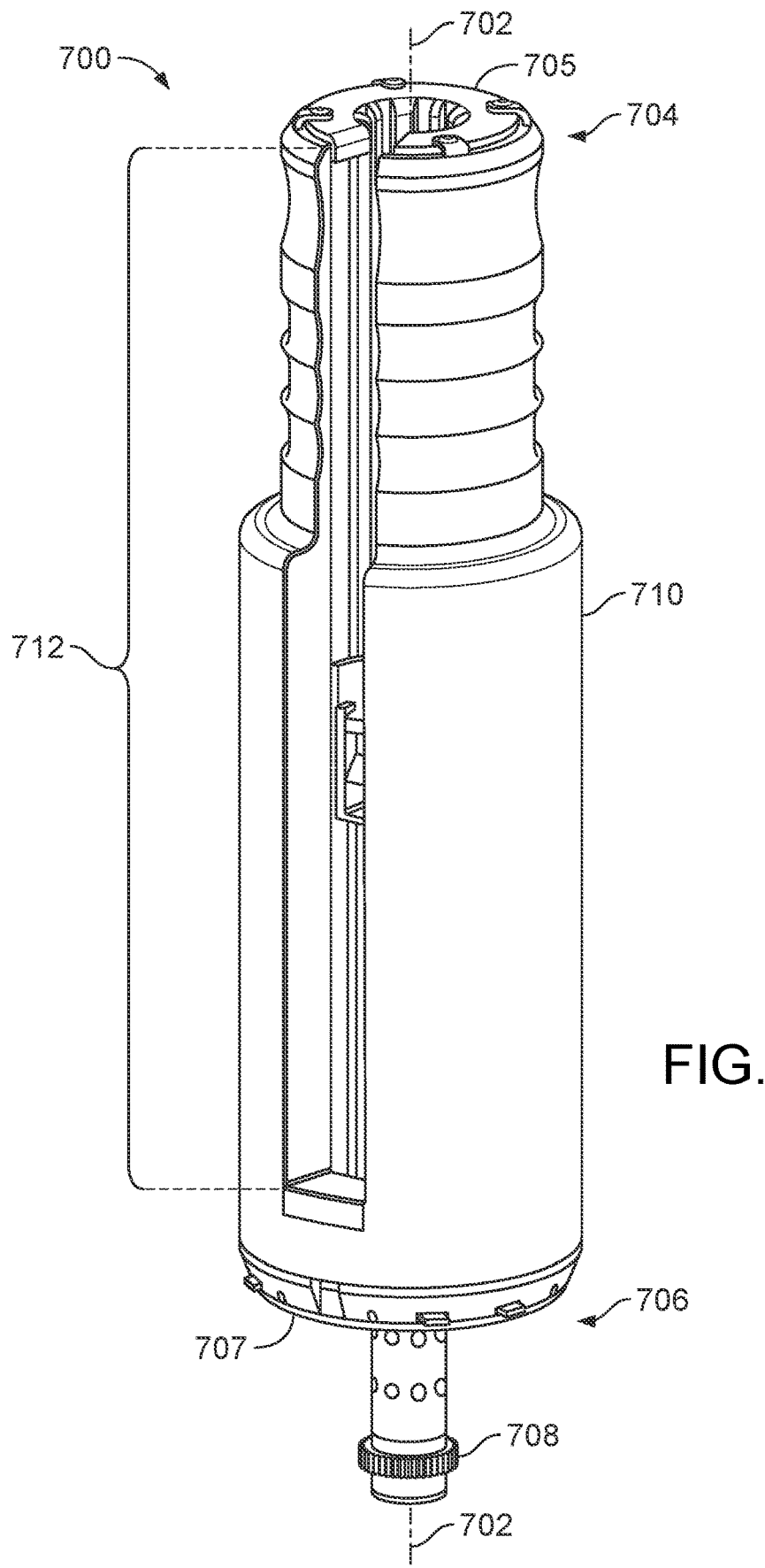
FIG. 9 is a perspective view of an example surgical instrument actuator in accordance with some embodiments.

Referring also to FIG. 9, an example surgical instrument actuator surgical instrument actuator 700 is shown in isolation from the surgical instrument 600 and the manipulator device 800. The example surgical instrument actuator 700 includes a proximal end 704 and a distal end 706. The surgical instrument actuator 700 defines the longitudinal axis 702 along which a surgical instrument (or other device such as an endoscopic camera) can be installed.

In the depicted embodiment, the surgical instrument actuator 700 includes a proximal end plate 705, a distal end plate 707, and a housing 710. The housing 710 extends between the proximal end 704 and the distal end 706.

In the depicted embodiment, the proximal end plate 705 is a c-shaped plate, while the distal end plate 707 is a fully circumferential plate that defines an open center. The opening in the proximal end plate 705 aligns with a slot opening 712 defined by the housing 710. The slot opening 712 and the opening in the c-shaped proximal end plate 705 provide clearance for a handle 612 of the surgical instrument 600 to project radially from the housing 710 while the surgical instrument 600 is coupled with the instrument drive system 700.

In the depicted example embodiment, the surgical instrument actuator 700 also includes a roll driven gear 708 located at the distal end 706. The pod's roll driven gear 708 can mesh with and be driven by a roll drive gear coupled to a roll-adjustment motor of the instrument actuator coupling 840 when the surgical instrument actuator 700 is coupled with the manipulator device 800. When the roll driven gear 708 is so driven, the entire surgical instrument actuator 700 rotates or rolls about the longitudinal axis 702. When the surgical instrument 600 is engaged with the surgical instrument actuator 700, the surgical instrument 600 also rotates or rolls about the longitudinal axis 702 as the roll driven gear is driven by the roll drive gear of the instrument actuator coupling 840. Alternatively, in some embodiments, a roll-adjustment motor (to which a roll drive gear is coupled) is a component of the surgical instrument actuator 700, and a roll driven gear is a component of the instrument actuator coupling 840. The roll driven gear can be fixed to the instrument actuator coupling 840 in some embodiments. In such an arrangement, when the roll driven gear is driven by the roll-adjustment motor, the entire surgical instrument actuator 700 rotates or rolls about the longitudinal axis 702.

Figure 10:
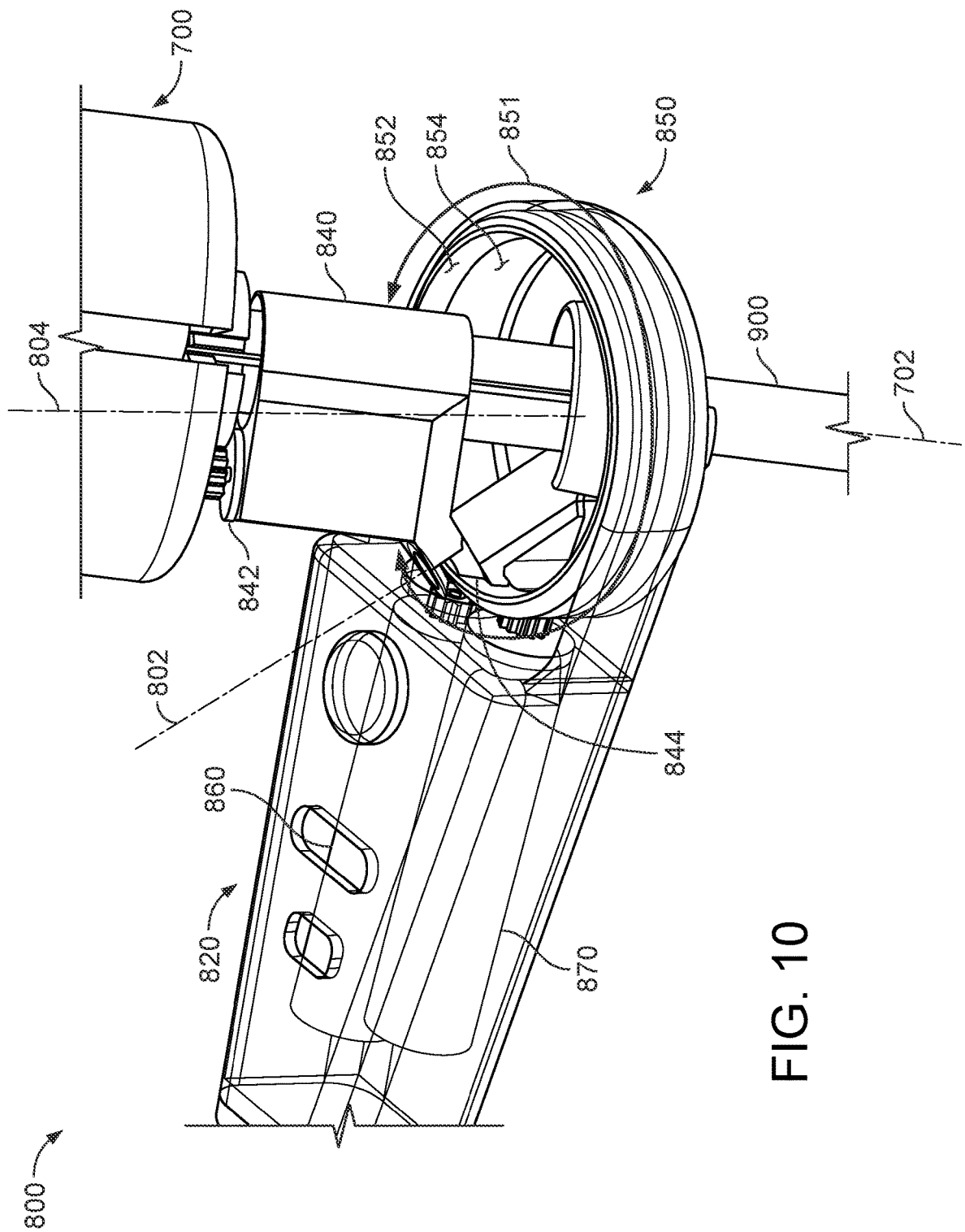
FIG. 10 is a perspective view of a distal end portion of an example computer-assisted tele-operated surgery manipulator device in accordance with some embodiments.

Referring also to FIG. 10, an enlarged view of a distal end portion of the example manipulator device 800 is shown, with the surgical instrument actuator 700 and the cannula 900 coupled thereto. The manipulator device 800 includes the arm 820 (shown transparently), the instrument actuator coupling 840, and the pair of concentric rings 850. The manipulator device 800 is configured to releasably couple with a set-up structure of a computer assisted tele-operated surgery system (such as the set-up structure 172 of FIG. 4), and to be controlled by a surgeon (e.g., using the surgeon console 40 and processor 43 as described in reference to FIG. 2).

The pair of concentric rings 850 include a first ring 852 and a second ring 854. The first ring 852 and the second ring 854 are arranged concentrically to each other such that they share a central axis 804 that passes through a center of the rings 852 and 854, and is perpendicular to the planes within which the rings 852 and 854 reside.

The first ring 852 and the second ring 854 are rotatable as indicated by arrow 851. Moreover, the first ring 852 and the second ring 854 are also individually rotatable, such that the rings 852 and 854 are rotatable in relation to each other. Rotations of the rings 852 and 854 can be driven jointly (together at the same speed, direction, and degrees of rotation) or differentially (at different speeds or degrees of rotation).

The manipulator device 800 includes a first drive motor 860 and a second drive motor 870. The first drive motor 860 drives rotations of the first ring 852. The second drive motor 870 drives rotations of the second ring 854. The drive motors 860 and 870 can be controlled (e.g., individual motor movements, speeds, and directions of rotation can be adjusted) to cause the rings 852 and 854 to manipulate the surgical instrument 600 as desired (e.g., using the surgeon console 40 and processor 43 as described in reference to FIG. 2).

In the depicted embodiment, the motors 860 and 870 drive the rings 852 and 854, respectively, through power trains that include one or more gears. In some embodiments, the motors 860 and 870 drive the rings 852 and 854, respectively, using one or more belts or cables.

When the rings 852 and 854 are driven by the motors 860 and 870 jointly (together at the same speed, direction, and degrees of rotation), the instrument actuator coupling 840 (and the surgical instrument actuator 700 and the surgical instrument 600) rotates around, or sweeps along, a cone centered of the central axis 804 of the rings 852 and 854 with the apex of the cone at the remote center of motion 502 (see FIG. 8). When the rings 852 and 854 are driven by the motors 860 and 870 differentially (e.g., at individually differing speeds, directions, or degrees of rotation), the tilt of the instrument actuator coupling 840 (and the surgical instrument actuator 700 and the surgical instrument 600) is adjusted around the tile axis 802, or sweeps along a cone centered on the tilt axis 802 with the apex of the cone at the remote center of motion 502.

Figure 11:
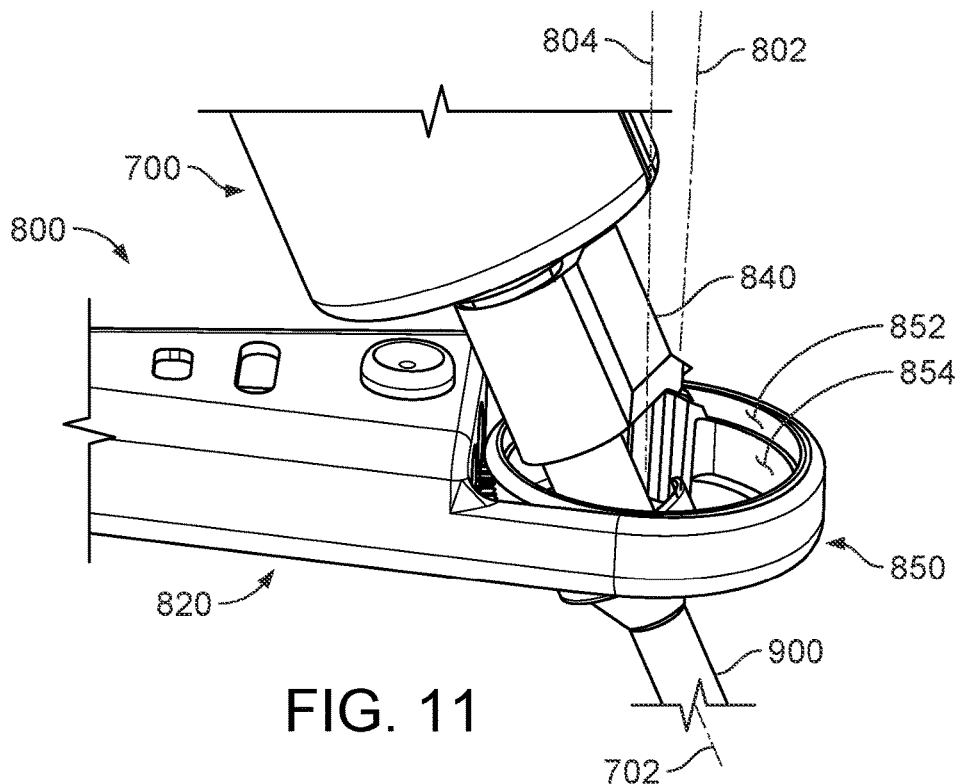
FIG. 11 is a perspective view of the manipulator device of FIG. 10 in another orientation.
Figure 12:
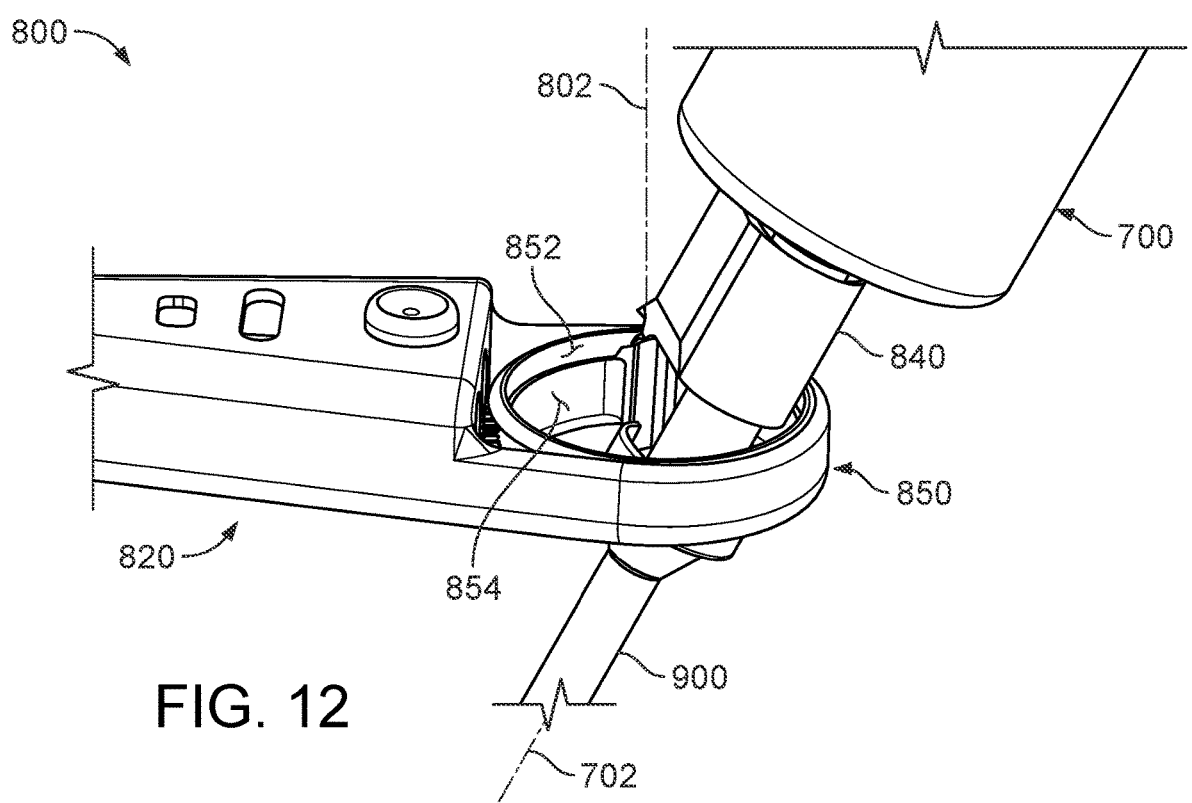
FIG. 12 is a perspective view of the manipulator device of FIG. 10 in yet another orientation.

Referring to the example configurations of FIGS. 11 and 12, when the second ring 854 is maintained in a stationary position relative to the arm 820 while the first ring 852 is rotated relative to the arm 820 (and relative to the second ring 854), the tilt of the instrument actuator coupling 840 (and the surgical instrument actuator 700 and the surgical instrument 600) in relation to the central axis 804 of the rings 852 and 854 is changed about the tilt axis 802 (e.g., as illustrated by comparing FIGS. 11 and 12).

In the depicted embodiment, the instrument actuator coupling 840 is pivotably coupled to the second ring 854. Hence, the instrument actuator coupling 840 can pivot about the tilt axis 802 in relation to the second ring 854. In addition, the instrument actuator coupling 840 includes an integral bevel gear 844 (see FIG. 10) that is meshed with internal gear teeth on an inner diameter of the first ring 852. Accordingly, when the rings 852 and 854 rotate relative to each other, the gear 844 of the instrument actuator coupling 840 and the internal gear teeth on the first ring 852 facilitates changes to the tilt of the instrument actuator coupling 840 (about the tilt axis 802) as a result of the relative movements between the rings 852 and 854.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-assisted tele-operated surgery manipulator, comprising:
    an arm configured to releasably couple with a set-up structure of a computer-assisted tele-operated surgery system;
    a first ring coupled to the arm;
    a second ring coupled to the arm; and
    a computer-assisted tele-operated surgical instrument actuator pivotably coupled to the second ring about a tilt axis,
    wherein relative movement between the first ring and the second ring adjusts the tilt axis.

2. The manipulator of claim 1, wherein the first ring and the second ring are each rotatably coupled to the arm.

3. The manipulator of claim 2, wherein the first ring and the second ring are arranged concentrically.

4. The manipulator of claim 2, further comprising a first ring drive motor coupled to drive rotations of the first ring and a second ring drive motor coupled to drive rotations of the second ring.

5. The manipulator of claim 1, further comprising an instrument actuator coupling configured to releasably couple with a computer-assisted tele-operated surgical instrument actuator and defining an instrument insertion axis.

6. The manipulator of claim 5, wherein the instrument actuator coupling is
pivotably coupled to the second ring about a tilt axis that is canted in relation to: (i) the insertion axis and (ii) a central axis shared by the first ring and the second ring.

7. The manipulator of claim 6, wherein the tilt axis and the central axis shared by the first ring and the second ring intersect at a remote center of motion point.

8. The manipulator of claim 7, wherein the remote center of motion point remains fixed in space at all possible rotational orientations of the first ring and the second ring.

9. The manipulator of claim 6, wherein differential relative rotations of the first ring versus the second ring drive pivoting of the instrument actuator coupling about the tilt axis.

10. The manipulator of claim 5, wherein the instrument actuator coupling includes a roll-adjustment motor for rotatably driving a computer-assisted tele-operated surgical instrument actuator about the instrument insertion axis.

11. The manipulator of claim 5, further comprising a surgical instrument actuator that is releasably coupleable with the instrument actuator coupling.

12. The manipulator of claim 11, further comprising a surgical instrument releasably coupleable with the surgical instrument actuator.

13. The manipulator of claim 5, wherein the instrument actuator coupling comprises a bevel gear that is meshed with internal gear teeth on an inner diameter of the first ring.

14. The manipulator of claim 1, wherein the second ring is configured to releasably couple with a cannula configured for providing surgical access through a patient's body wall during surgery using the computer-assisted tele-operated surgery manipulator.

15. The manipulator of claim 14, further comprising the cannula.

16. The manipulator of claim 1, further comprising the set-up structure, and wherein the set-up structure comprises a bracket with one or more joints.

17. The manipulator of claim 1, wherein the first ring and the second ring share a central axis.

18. The manipulator of claim 17, wherein the central axis is perpendicular to a plane in which the first and second rings reside.

* * * * *

UNITED STATES PATENT AND TRADEMARK OFFICE
CERTIFICATE OF CORRECTION

PATENT NO. : 12,042,238 B2  
APPLICATION NO. : 18/073026  
DATED : July 23, 2024  
INVENTOR(S) : Ryan Charles Abbott Page 1 of 1

It is certified that error appears in the above-identified patent and that said Letters Patent is hereby corrected as shown below:

On the Title Page

Below item (63) insert -- (60) Provisional application No. 62/541,320, filed on Aug. 4, 2017. --.

Signed and Sealed this  
Fifteenth Day of April, 2025

Coke Morgan Stewart  
*Acting Director of the United States Patent and Trademark Office*